United States Patent
Gracey et al.

(10) Patent No.: US 6,465,683 B2
(45) Date of Patent: Oct. 15, 2002

(54) PROCESS FOR MAKING N-BUTYL ESTERS FROM BUTADIENE

(75) Inventors: Benjamin Patrick Gracey; Norbert Walter Josef Kamp, both of Hull (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/844,438

(22) Filed: Apr. 30, 2001

(65) Prior Publication Data

US 2002/0049351 A1 Apr. 25, 2002

Related U.S. Application Data

(63) Continuation of application No. PCT/GB99/03452, filed on Oct. 19, 1999.

(30) Foreign Application Priority Data

Oct. 30, 1998 (GB) .............................................. 9823853

(51) Int. Cl.$^7$ .......................... C07C 67/04; C07C 67/00
(52) U.S. Cl. ...................................... 560/241; 560/247
(58) Field of Search ................................. 560/241, 247

(56) References Cited

U.S. PATENT DOCUMENTS

| | | | |
|---|---|---|---|
| 2,073,363 A | 3/1937 | Carothers et al. ............. | 260/33 |
| 3,919,294 A | 11/1975 | Onoda et al. ................ | 260/491 |
| 4,044,041 A * | 8/1977 | Stapp ......................... | 260/465 |
| 4,450,286 A | 5/1984 | Paxson ....................... | 560/241 |

FOREIGN PATENT DOCUMENTS

JP 9-194427 * 7/1997

OTHER PUBLICATIONS

Faith, Keyes, and Clark's Industrial Chemicals, 4$^{th}$ ed. John Wiley and Sons. pp. 173–177. (1975).*

The Merck Index, 9$^{th}$ ed. Merck & Co. p. 196. (1976).*

* cited by examiner

Primary Examiner—Mukund J. Shah
Assistant Examiner—Zachary C. Tucker
(74) Attorney, Agent, or Firm—Nixon & Vanderhye (57) ABSTRACT

Process for making a butyl ester from butadiene, comprising (a) reacting butadiene with a saturated aliphatic monocarboxylic acid to form a mixture of n-butenyl and secondary butenyl esters, (b) separating the n-butenyl ester from the secondary butenyl ester, and (c) hydrogenating the n-butenyl ester separated in step (b) in the presence of a catalyst to the corresponding n-butyl ester.

7 Claims, 6 Drawing Sheets

PROCESS FOR MAKING N-BUTYL ESTERS FROM BUTADIENE

This is a continuation of PCT application No. PCT/GB99/03452, filed Oct. 19, 1999, the entire content of which is hereby incorporated by reference in this application.

The present invention relates to a process for making n-butyl esters by reacting butadiene with a carboxylic acid in the presence of a Brønsted or Lewis acid catalyst to form the unsaturated ester which is subsequently hydrogenated to form the saturated ester.

BACKGROUND OF THE INVENTION

It is known that n-butyl esters such as n-butyl acetate can be produced by a number of routes. For instance, the hydroformylation of propylene in the presence of acetic acid is a method which gives a mixture of n-butyl acetate and iso-butyl acetate. This method however requires a source of syngas which increases capital costs. An alternative method is to react ethylene with vinyl acetate in the presence of an acid catalyst followed by the hydrogenation of the resultant unsaturated ester. A further method is the reaction of ethylene with ethanol in the presence of a base catalyst to form butanol and the reaction thereof with acetic acid to form butyl acetate. In addition, all these methods rely on the use of either relatively expensive feedstocks such as ethylene and n-butanol or involve multiple reaction stages or expensive catalysts and separation stages. The acid catalysed addition of butadiene to acetic acid using ion-exchangeresin catalysts having bulky counterions to improve the reaction selectivity to two isomeric $C_4$ butenyl acetates is disclosed in several patents viz., U.S. Pat. No. 4,450,288 (alkyl pyridinium), U.S. Pat. No. 4,450,287 (quaternary ammonium), U.S. Pat. No. 4,450,289 (quaternary phosphonium). The main objective of these patents is stated to be the production of secondary butenyl acetate. However, there is no mention in these documents of the isolation of n-but-2-enyl acetate or the production of n-butyl acetate. Butadiene is a relatively inexpensive by-product of the refining process and is a potential feedstock for making butyl esters. It is commercially available either as a purified chemical or as a constituent of a hydrocarbon cut. For example, as a constituent of a mixed $C_4$ stream obtained from naptha stream cracking. Typically such streams contain species such as butane, 1-butene, 2-butene, isobutane and isobutene in addition to butadiene. It is advantageous that a process utilising butadiene can use such streams. However, butadiene is also in equilibrium with 4-vinyl cyclohexene, a Diels Alder dimer of butadiene. This dimer can be thermally cracked back to butadiene:

So any process involving the use of butadiene as feedstock needs to take this reversible reaction into consideration.

EP-A-84133 describes a process for the production of unsaturated alcohols and/or esters of unsaturated alcohols. The reference describes the reaction between conjugated dienes and water or aqueous carboxylic acids. The resulting product, is a complex mixture of unsaturated isomeric alcohols and esters.

SUMMARY OF THE INVENTION

It has now been found that saturated n-butyl esters and secondary butyl esters can be synthesised without resort to either (a) the hydroformylation route from propylene or (b) the use of vinyl acetate or ethylene feedstocks in relatively simple stages.

According to a first aspect of the present invention, a process is provided for making a butyl ester from butadiene, this process comprising:

a. reacting butadiene with a saturated aliphatic monocarboxylic acid to form a mixture of n-butenyl and secondary butenyl esters, b. separating the n-butenyl ester from the secondary butenyl ester, and c. hydrogenating the n-butenyl ester separated in step b) in the presence of a catalyst to the corresponding n-butyl ester.

The butadiene employed in step a) may be employed in the form of a substantially pure butadiene. Alternatively, a hydrocarbon mixture comprising butadiene may be employed. In one embodiment a raw (e.g. crude or depleted) $C_4$ stream comprising butadiene, isobutene, 1 and 2-butenes and butane is employed. Such a stream may comprise up to 60% butadiene.

The secondary butenyl ester separated in step b) may be: i) recycled to step a), ii) hydrogenated in the presence of a catalyst to produce sec-butyl ester, iii) thermally cracked to produce the starting butadiene and a saturated aliphatic monocarboxylic acid; or iv) further reacted.

A preferred embodiment of the present invention is a process for making a butyl ester from butadiene, said process comprising:

a. reacting butadiene or a hydrocarbon fraction comprising butadiene with a saturated aliphatic monocarboxylic acid to form a mixture of n-butenyl and secondary butenyl esters, b. separating the n-butenyl ester from the secondary butenyl ester, c. recycling the secondary butenyl ester thus recovered to step a), and d. hydrogenating the n-butenyl ester in the presence of a catalyst to the corresponding n-butyl ester.

In the present process, the saturated, aliphatic carboxylic acid suitably has 1–6 carbon atoms and is preferably acetic acid. Thus, the present process can be readily adapted to the reaction of butadiene with acetic acid to form a mixture of n-butenyl acetate (also known as crotyl acetate) and secondary butenyl acetate, the latter being separated and preferably recycled to the initial stage and the n-butenyl acetate (crotyl acetate) being catalytically hydrogenated to form n-butyl acetate.

The reaction is suitably carried out in the liquid or mixed liquid/gas phase in the presence of a solvent. It is not essential that both reactants dissolve completely in the solvent. However, it is an advantage if the solvent chosen is such that it is suitably capable of dissolving both the reactants. Specific examples of such solvents include hydrocarbons such as decane and toluene and oxygenated solvents such as butyl acetate or excess carboxylic acid reactant and recycled higher esters such as $C_8$ acetates recycled sec-butenyl acetate. The use of excess carboxylic acid as a reactant can be advantageous when this chemistry is used to extract butadiene from an impure stream, as it facilitates reaction at high conversion of butadiene, or in process terms high efficiency of removal of butadiene. Currently the removal or recovery of butadiene from refinery streams requires a separate processing stage.

The reactions taking place in a preferred embodiment of the invention can be represented graphically by the following equation:

n-Butyl Carboxylate by the Addition of Carboxylic Acids to Butadiene

The reactions, and in particular, the addition reaction between butadiene and the carboxylic acid (step a), may be carried out using a homogeneous or heterogeneous catalyst. Heterogeneous catalysts may be advantageous in certain cases as they can facilitate the separation of the reaction product from the reaction mixture, and/or allow the catalyst to be conveniently separated from reaction by-products (mostly high boiling point butadiene oligomeric species). The preferred catalysts are based on strong acid ion-exchange resins (e.g. Amberlyst 15®, Amberlite IR120®) with a proportion of the acidic sites exchanged with bulky counterions such as tetra-phenylphosphonium counterions. Typically these counterions account for less than 10% of the available acidic sites.

The heterogeneous catalyst phase can be a partially or fully insoluble liquid phase (e.g. acidic ionic liquids, liquid acidic polymers and partially solvated polymers) or a solid (e.g. HY zeolite, strong acid macroreticular, macronet and gel ion-exchange resins and heteropolyacids of tungsten or molybdenum which have been ion-exchanged and/or supported on a carrier material). In addition to Amberlyst 15® mentioned above, other suitable examples of heterogeneous catalysts include fluorinated ion-exchange resins like Nafion®, phosphoric acid functionalised polymers, and acidic oxides such as HY zeolites.

In certain cases the activity of heterogeneous catalysts may decrease after prolonged periods of use. This may be due to blockage of active sites by butadiene oligo- and polymerisation products. In such cases, it may be advantageous to carry out the process of the present invention in homogeneous phase. Suitable homogeneous catalysts include sulphonic acids, triflic (trifluoromethanesulphonic) acid and its salts (triflates). Examples of such salts include lanthanide triflates, such as lanthanum trifluoromethanesulphonic acid salts. Suitable organic sulphonic acids include methane sulphonic acid, p-toluene sulphonic acid and sulphonated calixarenes. Heteropolyacids such as tungsten Keggin structure, strong acid ionic liquids such as those described in prior published EP-A-693088, WO 95/21872 and EP-A-558187 are also suitable.

The activity of the above mentioned heterogeneous catalysts can be modified by additives such as alkyl pyridinium, quaternary alkyl ammonium, quaternary arsonium and quaternary phosphonium compounds. These additives exchange with some of the acid sites on the support and to one skilled in the art can be introduced as a salt with a displaceable counterion e.g. halides, sulphates or carboxylates.

Levels of water may also play an important part in the activity of the catalyst. For example, water levels below 5% w/w are found to be preferable because at levels above 5% w/w the catalyst activity is significantly reduced. At levels below 0.01% w/w, however, the activity has also been found to be reduced. Consequently the water level in the reaction zone is suitably in the range from 0.01 to 5% w/w based on the carboxylic acid, preferably from 0.05 to 1% w/w.

The presence of water as a reaction adjuvant can also beneficially affect the selectivity of the catalyst. For example, when Amberlyst 15® is employed as a catalyst for the reaction between butadiene and acetic acid, the rate of reaction increases through a maximum as the concentration of water is increased. Thus, the reaction occurs at an optimum rate at a particular water concentration. Thus for the Amberlyst 15® catalysed reaction between butadiene and acetic acid, preferred water concentrations are about 0.2 to 0.5 w/w %, preferably 0.3 to 0.4 w/w %.

The reasons for this effect are not fully understood. However, without wishing to be bound by any theory, it is believed that water may have an effect on the accessibility of the active sites on the catalyst, the acidity of the catalyst and/or the hydrophilicity of the catalyst. It should be noted, however, that the effect of water on both the activity and selectivity of the catalyst may also be dependent on other factors, such as the nature of the catalyst and other reaction conditions employed.

In the process of the present invention it is also advantageous to use polymerisation inhibitors such as alkylated phenols (e.g. BHT butylated hydroxytoluene, also called 2,6-di-tert-butyl-p-cresol). Other members of this series include the Irganox® series of materials from Ciba Gigy, Lowinox® series of materials from Great Lakes Chemical Corporation, tropanol® series from ICI and t-butylcatechol, nitroxides and derivatives (e.g. di-t-butylnitroxide, and n,n-dimethyl-4-nitrosoaniline, nitric oxide), stable radicals (e.g. 2,2,6,6,-tetramethyl-piperidine-1-oxyl, 2,2,6,6,-tetramethyl-4-hydroxypiperidine-1-oxyl and 2,2,6,6,-tetramethylpyrrolidine-1-oxyl).

The relative mole ratios of butadiene to the carboxylic acid reactant in the addition reaction is suitably in the range from 5:1 to 1:50, preferably in the range from 1:1 to 1:10.

This addition reaction (step a)) is suitably carried out at a temperature in the range from 20 to 140° C., preferably from 20 to 130° C., more preferably, 30 to 120° C., and most preferably 40 to 90° C. The reaction is suitably carried out at the autogeneous reaction pressure which is determined by factors such as the reaction temperature, presence of absence of solvent, excess of reactants and impurities present in the butadiene stream. An additional pressure may be applied to the system if single fluid phase is preferred e.g. no butadiene gas phase in addition to the solvated liquid phase.

The addition reaction (step a)) may be suitably carried out in a plug flow reactor with the unused butadiene being flashed off and recycled to the reactor via a vapour liquid separator, but equally could be conducted in a slurry reactor.

In the case of a plug flow reactor, the butadiene can be present partially as a separate gas phase as well as being dissolved and this would result in either a trickle bed operation or a bubble bed operation. A typical LHSV (liquid hourly space velocity=volume of liquid feed/catalyst bed volume) for the carboxylic acid is 0.1 to 20 more preferably 0.5 to 5. In the case of a slurry reactor, a continuous bleed of any deactivated catalyst can be taken. In this case it is economically advantageous to run with catalyst in a various stages of deactivation to improve the utilisation of catalyst. This may result in the total loading of catalyst (activated+ deactivated) reaching high levels such as 50% w/w of the reaction charge.

Preferably, the butadiene may be added gradually to the saturated aliphatic monocarboxylic acid, for example, by multiple injection at constant pressure in a batch reactor. By adding the butadiene gradually in this manner, side reactions leading to, for example, the polymerisation of the butadiene can be minimised.

In the process, distillation is suitably used to allow separation of the reactants and products. A small amount of water azeotroping of reaction products may occur due to the low levels of water employed. However, this is minor and does not significantly effect the separation of the isomeric butenyl esters, i.e. the n-butenyl ester and secondary butenyl ester (step b)). The sec-butenyl ester can be recovered and recycled to the initial addition reaction between butadiene and the carboxylic acid (step c)). It has been found that the sec-butenyl ester under reaction conditions interconverts with butadiene, free carboxylic acid and the crotyl ester. The conversion of the sec-butenyl ester to free carboxylic acid and butadiene can be achieved by treatment in the vapour phase with an acidic support such as silica-aluminas. The use of such a separate pretreatment prior to the return to the carboxylic acid and butadiene to the addition reactor may have a beneficial effect on productivity and selectivity.

The separated n-butenyl ester stream is then passed to the catalytic hydrogenation stage (step d)) to form the n-butyl ester. It is preferable to carry out the hydrogenation step under heterogeneous conditions so that it is easy to separate the catalyst from the reaction products. The catalytic hydrogenation step is suitably carried out using one or more of the following catalysts: transition metal catalysts, typically from the later groups such as ruthenium, platinum, nickel, palladium, preferably supported on a low acidity carrier such as carbon or coating a support so that little free acidity remains. Examples include Raney nickel, supported Raney nickels, 5% ruthenium on carbon.

The preferred hydrogenation catalysts are a Raney nickel catalyst supported on carbon and a ruthenium catalyst also supported on carbon.

This hydrogenation (step d)) is suitably carried out at a temperature in the range of from 80 to 250° C., preferably, in the range of from 120 to 200° C. This stage can be conducted at elevated, atmospheric or sub-atmospheric pressures. The hydrogenation reaction is suitably carried at a pressure in the range from 1 barg to 100 barg, preferably from 5 to 50 barg. The hydrogenation can be carried out in slurry and flow reactors. If some carboxylic acid from the previous process stages is present, this can have a detrimental effect on some catalysts e.g. nickel catalysts can dissolve to give nickel acetates. This can limit the selection of the catalyst. A solvent is not required for this reaction. The reaction can be carried out in an all gas/vapour phase or as a two phase mixture. In the latter case, a flow reactor would be operated in either a trickle bed or a bubble bed mode. The completion of the hydrogenation of the n-butenyl esters can be determined conveniently for batch reactions by cessation of hydrogen uptake and in the case of both flow and batch reactors by sampling and analysis by methods such as Gas Chromatography and UV.

The process of the present invention has the following advantages:

i. The addition of butadiene to carboxylic acids may provide an attractive alternative to hydroformylation as a source of n-butyl esters. There is a significant feedstock cost advantage to the new process.

ii. The proposed $C_4$ butadiene based routes have an advantage over a propene-based routes when propene feedstock costs are high.

ii. In this process, impure butadiene streams can be used and this could further reduce feedstock costs and aid in refinery integration.

BRIEF DESCRIPTION OF THE DRAWINGS

The present invention is further illustrated with reference to the accompanying drawings, in which.

DETAILED DESCRIPTION OF THE PREFERRED EMBODIMENTS

Figure 1:
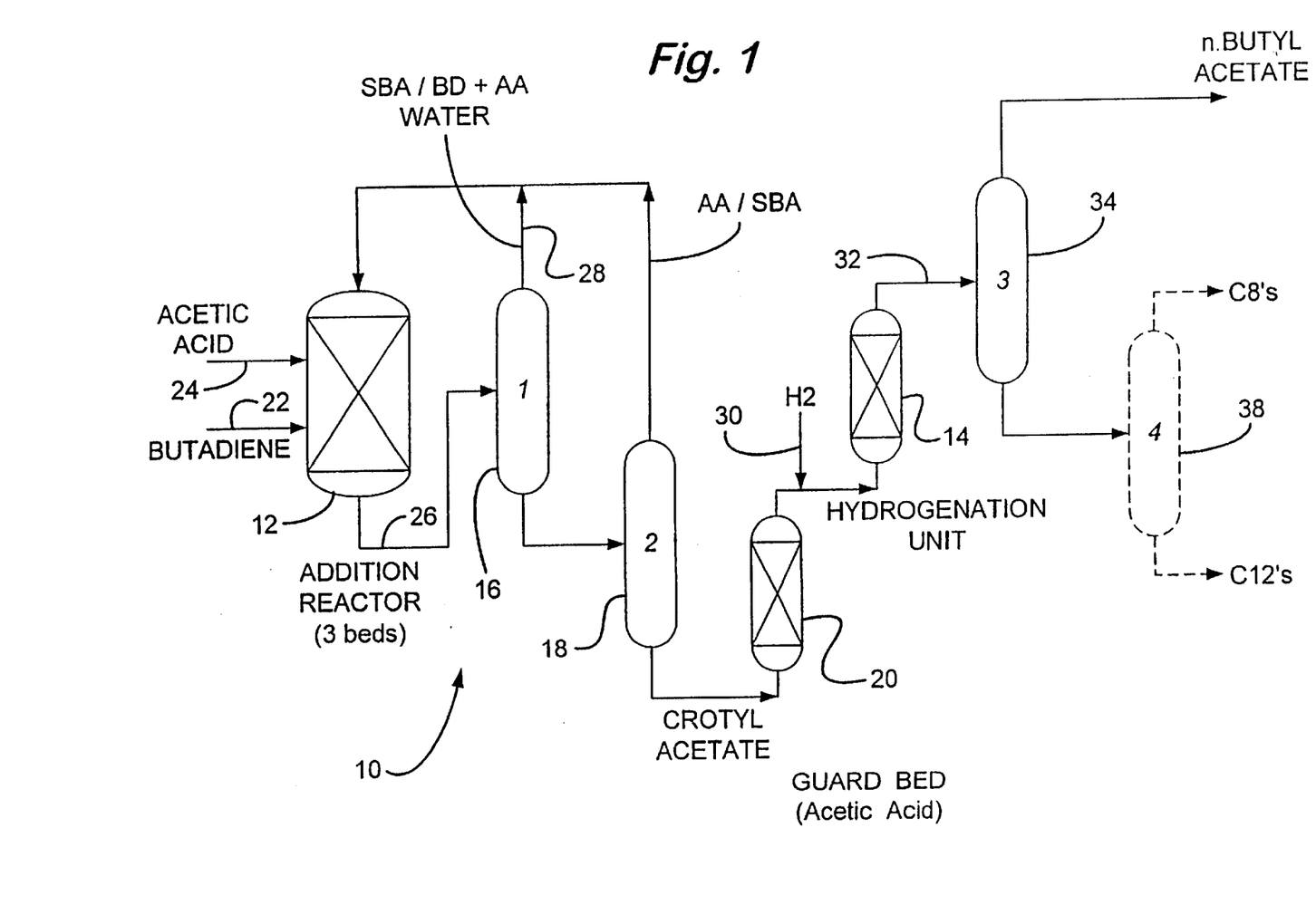
FIG. 1 is a schematic diagram of the apparatus suitable for carrying out a first embodiment of the present invention and FIG. 2 is a schematic diagram of the apparatus suitable for carrying out a second embodiment of the present invention.

Reference is first made to FIG. 1, which depicts an apparatus 10 suitable for the production of n-butyl acetate from a substantially pure butadiene feedstock. The apparatus 10 comprises an addition reactor 12, which is coupled to a hydrogenation unit 14 via a pair of distillation columns 16, 18 and a guard bed 20 for the removal of acetic acid. The addition reactor 12 comprises three fixed beds (not shown).

In operation, butadiene and acetic acid are fed into the addition reactor 12 via lines 22, 24. The reactants react to produce a product stream 26 comprising sec-butenyl acetate and crotyl acetate. Unreacted materials, such as butadiene, acetic acid and water (as an azeotrope) are also present in the product stream 26.

The product stream 26 is introduced into column 16, which separates the water, unreacted butadiene, some unreacted acetic acid and some sec-butenyl acetate from the remainder of the product stream 26. The water, unreacted butadiene, some unreacted acetic acid and some sec-butenyl acetate are recovered from the top of the distillation column 16 as an overhead stream, and recycled to the addition reactor 12 via line 28. In an alternative embodiment (not shown), the overhead stream is decanted to adjust the amount of water recycled. In a further alternative (not shown), the overhead stream is cracked, so as to convert the secondary butenyl acetate back to butadiene and acetic acid.

A stream consisting essentially of crotyl acetate, sec-butenyl acetate and acetic acid is recovered from the base of the column 16 and introduced into the second distillation column 18. The column 18 separates the remainder of the secondary butenyl acetate and acetic acid from the crotyl acetate. The secondary butenyl acetate and acetic acid are recycled back to the addition reactor 12 via the top of the column 18, whilst the crotyl acetate is removed from the base of the column 18 and introduced into the guard bed 20. The bed 20 removes any traces acetic acid that may still be present in the crotyl acetate stream.

The crotyl acetate, substantially free of acetic acid, is then introduced into the hydrogenation unit 14. Hydrogen is introduced into the unit 14 via line 30, and the ensuing reaction produces a product stream 32 comprising impure n-butyl acetate.

The stream 32 is recovered from the hydrogenation unit 14 and introduced into a third distillation column 34 for purification. The column 34 removes $C_8$ and $C_{12}$ acetate that may be produced as by-products. The $C_8$ and $C_{12}$ by-products may be separated from one another using a further distillation column 38.

Figure 2:
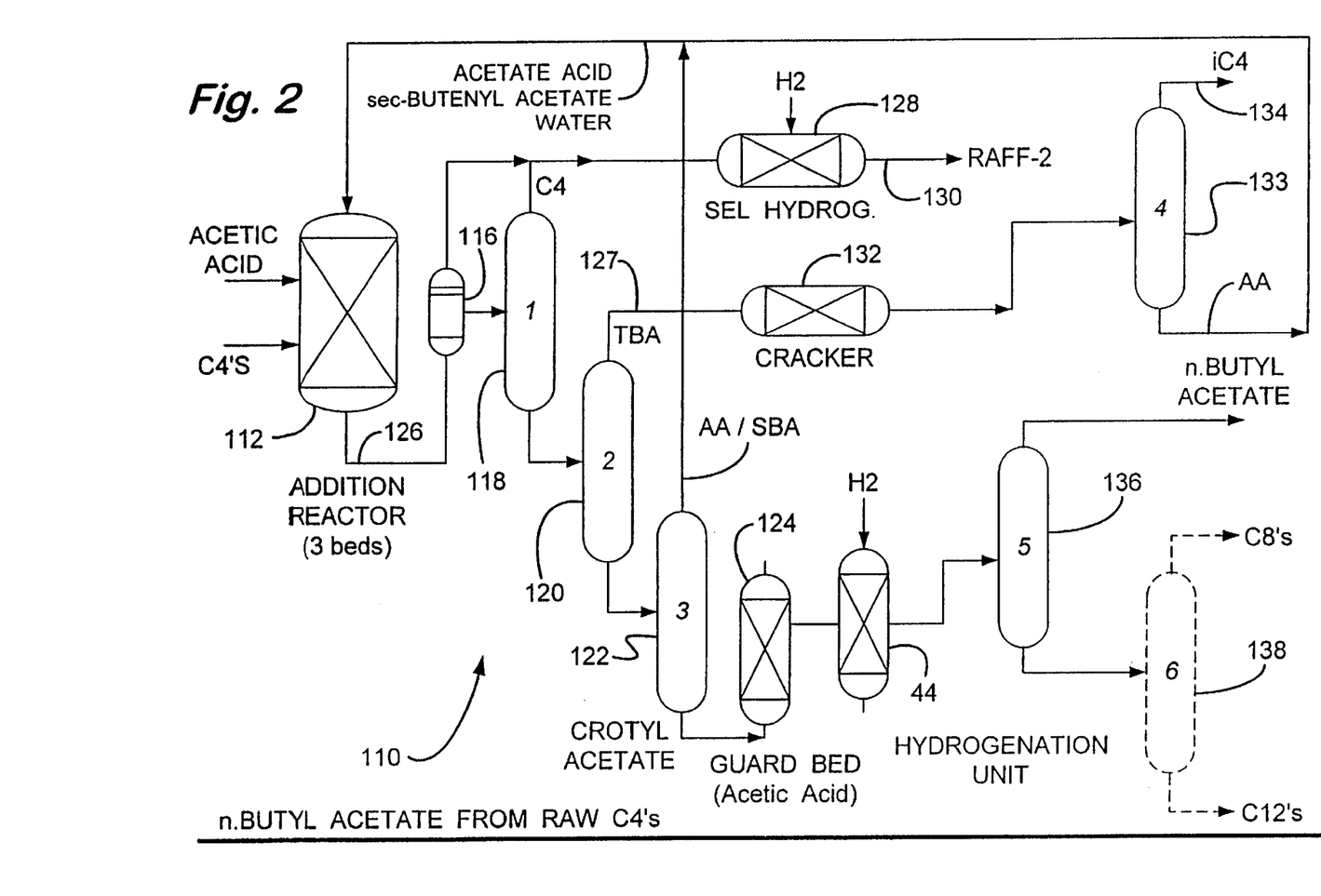

Reference is now made to FIG. 2, which depicts an apparatus suitable for carrying out a second embodiment of the present invention. The apparatus 110 is similar to the apparatus 10 depicted in FIG. 1. However, whereas the apparatus 10 of FIG. 1 is adapted for use with a substantially pure butadiene feedstock, the apparatus 110 of FIG. 2 is adapted for use with a mixed $C_4$ feedstock comprising butadiene, butane, isomeric butenes and isobutane.

The apparatus 110 comprises an addition reactor 112 which is coupled to a hydrogenation unit 114, via a flash drum 116, a series of distillation columns 118, 120, 122, and a guard bed 124.

In operation, acetic acid and a mixed $C_4$ stream are introduced into the addition reactor 112. The ensuing reaction produces a product stream 126 which comprises unreacted starting materials and a mixture of addition products including n-butenyl acetate, sec-butenyl acetate, and t-butyl acetate.

The product stream 126 is removed from the addition reactor 112 and introduced into the flash drum 116, which separates the most volatile components from the remainder of the product stream 126. These volatile components include a mixture of butane, isomeric butenes, butadiene, isobutene and butadiene. By hydrogenating this mixture under mild conditions in reactor 128, the traces of butadiene present are hydrogenated to butene. The resulting product 130 is suitable for sale.

The less volatile remainder of the product stream 126 is then introduced into the first of the distillation columns 118, which further purifies the stream by removing the traces of butane, isomeric butenes, butadiene, isobutene and butadiene, not previously removed by the flash drum 116.

Thus purified, the stream 126 is introduced into the second distillation column 120, which separates the t-butyl acetate 127 from remainder of the stream 126. The t-butyl acetate 127 is removed from the top of the distillation column 120, and introduced into a thermal cracker 132, which cracks the t-butyl acetate into iso-butene and acetic acid. These compounds are separated and recovered using a distillation column 133. The isobutene recovered 134 is substantially pure, and is suitable for direct use or further processing. The acetic acid recovered is recycled back to the addition reactor 112.

The stream recovered from the base of the distillation column 120 is introduced into a third distillation column 122. This distillation column 122 separates the acetic acid and sec butenyl acetate from the crotyl acetate. The acetic acid and sec-butenyl acetate are recovered from the top of the column 122, and recycled back to the addition reactor 112. The impure crotyl acetate is removed from the base of the column 122, and introduced into the guard bed 124, which purifies the crotyl acetate by removing any traces of acetic acid that may be present.

The acid-free crotyl acetate is then hydrogenated in the hydrogenation unit 114 to produce a product stream comprising impure n-butyl acetate. The stream is purified in distillation column 136, which removes any $C_8$ acetates and other by-products that may be present. These by-products may be removed from the base of column 136 and separated using a further distillation column 138.

EXAMPLES

Examples of Stage (A) Reaction of Butadiene with Acetic Acid General Method for Preparation of Feeds and Autoclave Reaction The following apparatus was used in batch mode to conduct the addition reaction of acetic acid to butadiene. A 10 L stainless steel autoclave equipped with a high efficiency impeller type stirrer and LPG handling facility was used for these experiments. The autoclave had mounted within it a fine mesh stainless steel bag in the form of a stationary annulus around the stirrer. This was used to contain the catalyst and prevent attrition during stirring. It also served to facilitate multiple reactions involving the same catalyst. The autoclave was also equipped with a sampling valve arrangement which allowed retrieval of samples during the course of the reaction.

The following general method was used for the reactions. The ion-exchange resin was pre-cleaned of extractable materials by use of a Soxhlet extraction apparatus. A range of solvents were used depending upon the nature of the resin. For example, with gel type strong acid resins, acetic acid or methanol were used and the resin was charged to the autoclave in the wet form. For macrorecticular type resins, methanol was used as the solvent and the cleaned resin was then dried in a stream of nitrogen prior to use. In the case of cation exchanged resin samples, the resin was pre-treated as described above by a Soxhlet extraction and then the resin was used wet (pre-swelled) to exchange with an acetic acid solution of the target cation salt. This was achieved by stirring the solution with the resin in glassware for 16 hrs before replacing the resin in the Soxhlet extractor and repeating the extraction with methanol or another suitable solvent. The cleaned exchanged resin was then dried in a nitrogen stream prior to use. The resin to be tested was then weighed and charged to the stainless steel bag mentioned previously.

The autoclave was then sealed, pressure tested with a nitrogen pressure and pressure-purged of any residual oxygen. The acetic acid feed was subjected to a Karl Fischer water analysis (water level of 0.2% w/w±0.05 except where specified otherwise). The water level in this feed was modified to the experimental target level either by pretreatment with acetic anhydride (strong acid ion-exchange resin used as a catalyst removable by filtration prior to use) or by adding water. The acetic acid was also purged with nitrogen prior to use to remove dissolved oxygen. The acetic acid charge to the autoclave was used also to solubilise and add any di-tert-butyl hydroxy toluene inhibitor or other trial additive.

The acetic acid charge was added to the autoclave via a funnel, the autoclave was then pressure-purged with nitrogen and heated to the reaction temperature with stirring, at which point the butadiene charge was added to the autoclave as a liquid by forcing the material in from a weighed storage vessel with a nitrogen pressure. The point of this addition was taken as t=0 and the stirred autoclave contents were sampled at regular intervals and analysed by flame ionisation detector (FED) Gas chromatography (GC). Due to problems associated with loss of volatile butadiene from the autoclave samples it was found to be advantageous to add 0.1–1% w/w on the acetic acid charge of decane as an internal standard. Control experiments with and without this added decane demonstrated that there was no significant effect on the progress of the reaction. The identity of the GC peaks was established by the synthesis of model compounds and GC/MS. The GC was calibrated by means of the purchase and synthesis of pure compounds i.e. acetic acid, butenyl acetate, sec-butenyl acetate, and 4-vinyl cyclohexene. The higher boiling by-products from the reaction were assigned the same response factor determined for butenyl acetate and thereby roughly quantified. All these higher boiling point material peaks were combined together—designated "highers"—and the calculated % w/w used to calculate the reaction selectivity.

Example 1
Use of Amberlyst® 15H Resin without Pre-treatment

The general method described above was used except that the Amberlyst 15H® resin was used without any purification.
Charge to autoclave
Amberlyst 15H® (unwashed)—85 g
Acetic acid—3600 g
1,3-butadiene—1400 g
Reaction conditions: 60° C. with stirring at 1200 rpm Example 1

| Runtime (Hours) | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 1.3 | 0 |
| 5 | 7.7 | 7.59 | 1.3 | 2.85 |
| 6 | 8.95 | 9.37 | 1.28 | 3.91 |
| 7 | 9.49 | 10.24 | 1.25 | 4.34 |
| 8 | 10.49 | 11.72 | 1.26 | 5.07 |
| 24 | 10.98 | 14.21 | 0.77 | 6.55 |

These results illustrate that the reaction proceeds to give predominantly the isomeric $C_4$ acetates and that some loss of selectivity occurs to higher boiling point materials particularly at high reaction times. The reaction product was pale yellow which darkened on standing.

Example 2
Use of Amberlyst 15H® Resin with Pre-conditioning

The general method was used and the resin washed with ethyl acetate and dried prior to use. The following components were charged to the autoclave:
Amberlyst 15H®—85 g
Acetic acid—3600 g
1,3-Butadiene—700 g
Reaction conditions: 50° C., with stirring at 1200 rpm Example 2

| Runtime (Minutes) | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 1.39 | 0 |
| 30 | 1.08 | 0.72 | 1.31 | 0.21 |
| 60 | 1.97 | 1.37 | 1.34 | 0.45 |
| 90 | 2.83 | 2.02 | 1.35 | 0.71 |
| 150 | 4.01 | 3.1 | 1.31 | 1.2 |
| 210 | 5.3 | 4.37 | 1.26 | 1.75 |
| 270 | 6.2 | 5.43 | 1.19 | 2.26 |
| 330 | 6.96 | 6.36 | 1.19 | 2.71 |
| 390 | 7.92 | 7.58 | 1.2 | 3.09 |

These results reaffirm the previous results and demonstrate that the sec-butenyl acetate is the kinetic reaction product and that the n-butenyl acetate is the thermodynamic product. The reaction product was initially colourless but darkened on standing to a pale yellow. This illustrates that pre-treatment of the Amberlyst 15H® resin served to reduce the colour of the product.

Examples 3 and 4
Effect of Temperature on Reaction Rate

Two sequential reactions were carried out on the charge of 85 g of Amberlyst 15H® used in example 2 (ethyl acetate pre-washed), the catalyst between runs was washed with acetic acid in situ to remove residual material from the previous run in the sequential reactions. The charge of butadiene was 700 g and acetic acid was 3600 g for all three experiments.

Example 3 at 40° C.

| Runtime (Minutes) | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 1.39 | 0 |
| 60 | 0.77 | 0.64 | 1.44 | 0.16 |
| 90 | 1.01 | 0.77 | 1.44 | 0.25 |
| 150 | 1.55 | 1.15 | 1.4 | 0.36 |
| 210 | 2.24 | 1.62 | 1.37 | 0.53 |
| 270 | 2.63 | 1.91 | 1.36 | 0.64 |
| 330 | 3.32 | 2.44 | 1.36 | 0.86 |
| 390 | 3.89 | 2.89 | 1.39 | 1.04 |

Example 4 at 60° C.

| Runtime | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 1.39 | 0 |
| 60 | 3.19 | 2.62 | 1.3 | 0.9 |
| 90 | 4.13 | 3.55 | 1.26 | 1.32 |
| 150 | 6.16 | 6.02 | 1.18 | 2.63 |
| 210 | 7.44 | 7.89 | 1.14 | 3.77 |
| 270 | 7.92 | 8.71 | 1.13 | 4.25 |
| 330 | 8.39 | 9.56 | 1.1 | 4.96 |
| 390 | 8.63 | 10.18 | 1.07 | 5.43 |

Examples 2, 3 and 4 illustrate that an optimum balance exists between activity and selectivity, i.e. at higher temperatures the activity is increased at the expense of the reaction selectivity. The process optimum will vary with factors such as catalyst employed and feedstock costs.

Examples 5 and 6
Illustration of Catalyst Deactivation without Addition of Inhibitor The Amberlyst 15H® resin charge used in example 4 was re-used as described for examples 3 and 4 by washing in situ with acetic acid in between runs. The butadiene and acetic acid charge were kept substantially identical to that employed in example 2. Example 6 re-used the charge used in example 5.

Example 5 at 50° C.

| Runtime (Minutes) | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 1.39 | 0 |
| 60 | 0.96 | 0.84 | 1.41 | 0.31 |
| 90 | 1.34 | 1.1 | 1.51 | 0.4 |
| 150 | 1.98 | 1.55 | 1.51 | 0.55 |
| 210 | 2.44 | 1.89 | 1.44 | 0.71 |
| 270 | 3.22 | 2.5 | 1.47 | 0.94 |
| 330 | 3.72 | 2.91 | 1.44 | 1.14 |
| 390 | 4.53 | 3.6 | 1.52 | 1.34 |

Example 6 at 50° C.

| Runtime (Minutes) | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 1.39 | 0 |
| 150 | 1.57 | 1.05 | 1.56 | 0.33 |
| 270 | 2.87 | 2.01 | 1.49 | 0.74 |
| 330 | 3.22 | 2.3 | 1.46 | 1.86 |

Comparison of examples 2, 5 and 6 shows that catalyst deactivation occurred. The rate of deactivation is such that the conclusions drawn from examples 2, 3 and 4 are still valid.

Examples 7, 8. 9, 10 and 11

To Show that the Presence of an Inhibitor Reduces the Rate of Catalyst Deactivation The autoclave was charged with a fresh ethyl acetate-washed sample of Amberlyst 15H® resin (85 g) for example 7 and this was re-used in the subsequent examples (7 then 8 then 9 and then 10) by washing with acetic acid in situ as previously described. The inhibitor BHT (2.5 g) was dissolved in the acetic acid charge 3600 g prior to charging the autoclave. 700 g of butadiene was used in each example.

Example 7 at 50° C.

| Runtime (Minutes) | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 1.44 | 0 |
| 155 | 3.15 | 2.44 | 1.1 | 0.68 |
| 275 | 4.7 | 3.97 | 1.03 | 1.2 |
| 395 | 5.24 | 4.57 | 1.02 | 1.4 |

Example 8 at 50° C.

| Runtime (Minutes) | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 1.44 | 0 |
| 155 | 2.86 | 2.16 | 1.66 | 0.67 |
| 275 | 4.74 | 3.88 | 1.57 | 1.33 |
| 395 | 6.04 | 5.26 | 1.53 | 1.93 |

Example 9 at 50° C.

| Runtime (Minutes) | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 1.44 | 0 |
| 155 | 2.02 | 1.45 | 1.46 | 0.43 |
| 275 | 3.25 | 2.42 | 1.44 | 0.77 |
| 395 | 4.33 | 3.4 | 1.42 | 1.03 |

Example 10 at 50° C.

| Runtime (Minutes) | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 1.44 | 0 |
| 155 | 1.96 | 1.37 | 1.47 | 0.41 |
| 275 | 3.11 | 2.27 | 1.43 | 0.72 |
| 395 | 4.23 | 3.26 | 1.41 | 1.09 |

Example 11 at 50° C.

| Runtime (Minutes) | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 1.44 | 0 |
| 155 | 1.68 | 1.16 | 1.45 | 0.1 |
| 275 | 2.72 | 1.95 | 1.42 | 0.61 |
| 395 | 4.22 | 3.24 | 1.42 | 1.00 |

Comparison of examples 2 to 6 and 7 to 11 illustrates that the presence of inhibitor both decreases the rate of catalyst deactivation and also increases the reaction selectivity. A slight decrease in initial activity of catalyst is also observed.

Examples 12–14
To Illustrate the Effect of Water

Example 12

The general method was followed. The following charge was used:
Amberlyst 15H® (ethyl acetate washed)—85 g
Acetic acid—3600 g
Water—72 g
Butadiene—700 g
Reaction temperature 60° C. with stirring at 1200 rpm.
No conversion to the butenyl acetates was observed over 5 hrs.

Example 13

The catalyst from example 12 was reused, by pre-washing in situ with acetic acid. The same reaction conditions and charge were used except that the amount of added water was reduced to 36 g.

Example 13 at 60° C.

| Runtime (Minutes) | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 1.56 | 0 |
| 150 | 1.62 | 1.38 | 1.51 | 0.15 |
| 270 | 2.44 | 2.13 | 1.51 | 0.28 |

Example 14

The catalyst from example 13 was reused, by pre-washing in situ with aceticacid. The same reaction conditions and charge were used except that the amount of added water was reduced to 14 g.

| Runtime (Minutes) | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 1.37 | 0 |
| 150 | 3.7 | 3.01 | 1.32 | 0.78 |
| 270 | 5.62 | 5.02 | 1.24 | 1.52 |
| 390 | 7.52 | 7.25 | 1.24 | 2.3 |

Comparison of examples 12–14 illustrate that water is a reversible poison for the catalyst.

Examples 15, 16, 17 and 18
To Show the Effect of Low Levels of Water on Catalyst Deactivation Fresh Amberlyst 15H® resin (ethyl acetate washed, 85 g) was charged to the stainless steel bag. The catalyst was re-used in these examples (using an acetic acid wash in situ in between examples). The following charge was used:

Acetic acid (3600 g, pre-treated with acetic anhydride-content <0.01% w/w) water (0.052% w/w based on acetic acid)
BHT (3 g)
Butadiene (700 g)
Reaction temperature 50° C. with stirring at 1200 rpm.

Example 15 at 50° C.

| Runtime (Minutes) | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 0.507 | 0 |
| 150 | 2.64 | 2.068 | 0.478 | 0.487 |
| 270 | 3.729 | 3.174 | 0.468 | 0.788 |
| 390 | 4.675 | 4.34 | 0.465 | 1.139 |

Example 16 at 50° C.

| Runtime (Minutes) | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 0.424 | 0 |
| 170 | 1.972 | 1.499 | 0.43 | 0.354 |
| 270 | 3.229 | 2.634 | 0.43 | 0.69 |
| 390 | 4.193 | 3.685 | 0.43 | 1.017 |

Example 17 at 50° C.

| Runtime (Minutes) | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 0.41 | 0 |
| 150 | 1.76 | 1.252 | 0.542 | 0.31 |
| 285 | 2.776 | 2.144 | 0.416 | 0.577 |
| 390 | 3.487 | 2.87 | 0.42 | 0.8 |

Example 18 at 50° C.

| Runtime (Minutes) | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 0.43 | 0 |
| 150 | 1.298 | 0.851 | 0.43 | 0.204 |
| 270 | 2.107 | 1.478 | 0.43 | 0.377 |
| 390 | 2.836 | 2.131 | 0.43 | 0.580 |

Comparison of this set of examples with previous examples demonstrates that lower levels of water lead to an increased loss of reaction selectivity (selectivity to the isomeric $C_4$ acetates) and also an increased rate of deactivation of the catalyst.

Example 19
Use of Co-solvents and Counterions in the Reaction 4.5% of the acid sites on a sample of ethyl acetate-washed Amberlyst 15H® resin were exchanged with tetraphenyl phosphonium bromide by the method described previously. This material was charged to the autoclave with acetic acid (1700 g, 0.2% w/w water), ethyl acetate (900 g) and butadiene (700 g). The reaction was conducted in the usual manner at 50° C. with stirring at 1200 rpm.

Example 19 at 50° C.

| Runtime (Minutes) | sec-Butenyl acetate (% w/w) | n-Butenyl acetate (% w/w) | 4-Vinyl cyclohexene (% w/w) | Highers (% w/w) |
|---|---|---|---|---|
| 0 | 0 | 0 | 1.35 | 0 |
| 155 | 3.53 | 3.11 | 1.28 | 1.06 |
| 275 | 4.89 | 4.62 | 1.24 | 1.63 |
| 395 | 6.43 | 6.55 | 1.28 | 2.46 |

Example of Step (b)—Isolation of Crotyl Acetate from the Reaction Mixture

Example 20

The butadiene and excess acetic acid recovery stage was modelled. The crude recovery was modelled using a rotary evaporator (80% of reaction mixture taken overhead, ~500 mmHg pressure). The initial composition of the reaction mixture is shown below:

| Example | sec-Butenyl acetate (% w/w) | n-Butenyl acetate (% w/w) | 4-Vinyl cyclohexene (% w/w) | Highers (% w/w) |
|---|---|---|---|---|
| 20 | 6.43 | 6.55 | 1.28 | 2.46 |

Analysis of the overheads product (80%) by GC showed that it consisted of mainly acetic acid and sec-butenyl acetate with traces of other species such as 4-vinyl cyclohexene and water.

The remaining concentrate in the flask (20%) was transferred to a distillation apparatus equipped with a reflux splitter and 1.5 m long, 30 mm wide packed column. The apparatus was operated in batch mode with the following main fractions being collected in the following order:

Mixed fraction of sec-butenyl acetate and acetic acid with a trace amount of water (at 106–117° C.); and crotyl acetate (at 120–125° C.)

Examples of Step (c)—Recycle of Sec-butenyl Acetate

Example 21–25

To demonstrate the inter-conversion of the isomeric $C_4$ butenyl acetates, a Quickfit® glass apparatus was assembled consisting of a heated three-necked round-bottomed flask equipped with a condenser, an overhead stirrer, a sampling valve and a nitrogen top cover. The examples were carried out as follows:

The reaction flask was charged with Amberlyst15®, acetic acid and an internal standard (decane). This was allowed to equilibrate at the reaction temperature for 20 minutes. The $C_4$ butenyl acetates were added through a syringe in 6×10 ml doses over 3 minutes.

Samples from the reaction vessel were taken by syringe at regular intervals. Conversion of both crotyl acetate to sec-butenyl acetate and the corresponding reverse reaction of sec-butenyl acetate to crotyl acetate was monitored. An equilibrium between crotyl acetate and butenyl acetate was found, the reaction mixture tending to a 1:1.5 mixture of sec-butenyl:crotyl acetate under the reaction conditions. An acid catalyst was required to promote this reaction: no reaction was observed in the absence of a catalyst. Free butadiene was also observed in the GC trace. The presence of inhibitor was found to improve the selectivity of the inter-conversion.

| Ex. No. | Crotyl Acetate (g) | 2-Butenyl Acetate (g) | Acetic Acid (g) | Amberlyst 15 ® (g) | Atmosphere | Temp. (° C.) |
|---|---|---|---|---|---|---|
| 21 | 59.4 | 0.0 | 180.2 | 15.8 | Static $N_2$ | 50 |
| 22 | 0.0 | 60.8 | 183.3 | 15.8 | Static $N_2$ | 50 |
| 23 | 29.1 | 29.1 | 183.3 | 15.8 | Static $N_2$ | 50 |
| 24 | 60.0 | 0.0 | 183.3 | 15.8 | Static $N_2$ | 50 |
| 25 | 0.0 | 60.0 | 183.3 | 15.8 | Static $N_2$ | 50 |

Figure 3:
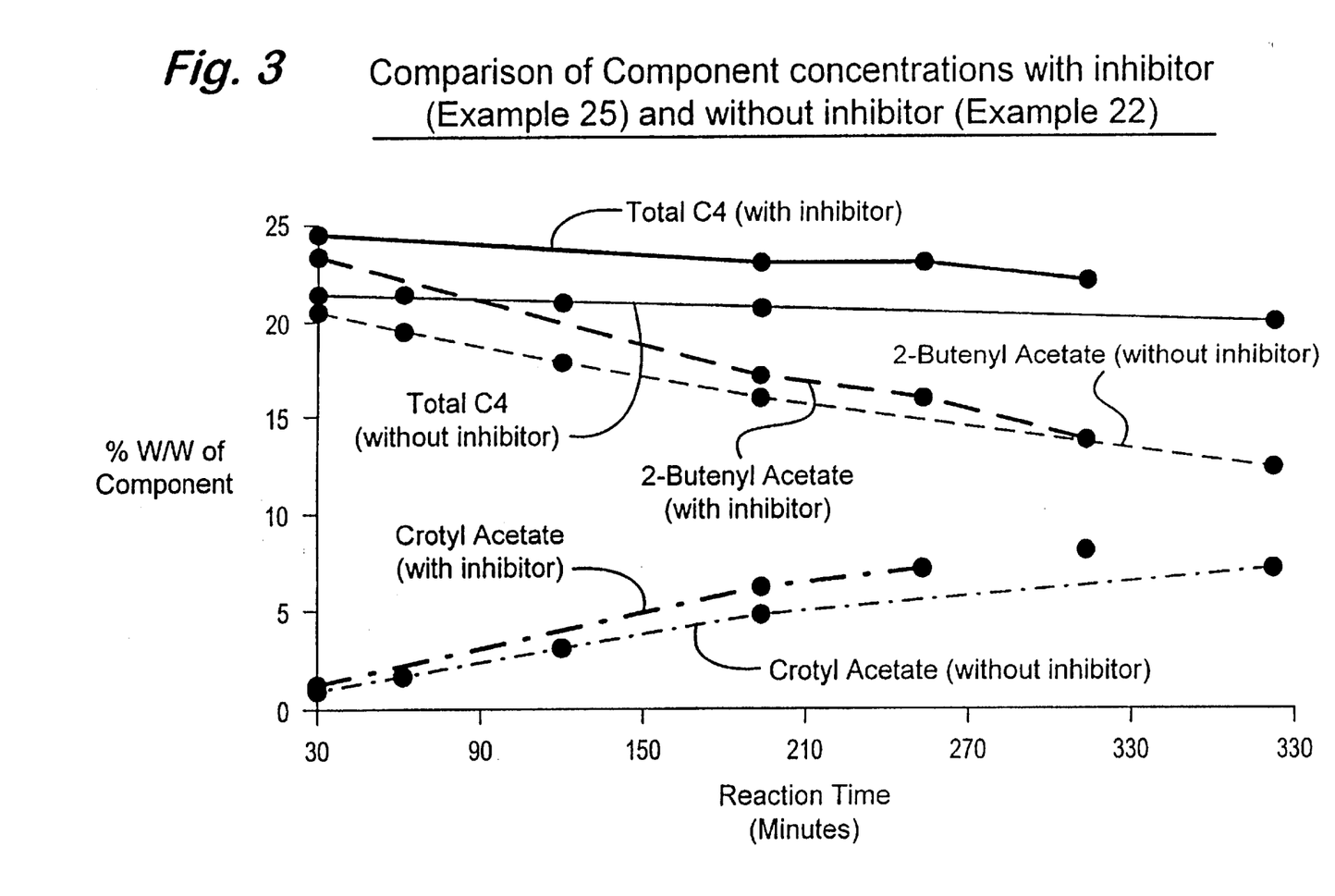
FIG. 3 is a graphical depiction of component concentrations with inhibitor and without inhibitor plotted against reaction time.

Examples 24 and 25 contained the inhibitor 2,6-Di-tert-butyl-4-methylphenol at 600 ppm FIG. 3 illustrates the re-equilibration of the two isomers (see below).

Step d) Hydrogenation of Crotyl Acetate to n-butyl Acetate

An initial charge of crotyl acetate (60.0 g), toluene (240.0 g), decane (3 g) and Raney nickel catalyst supported on carbon (ex Harshaw, ground to >60 mesh, 6.0 g) was charged to a stirred batch autoclave (500 ml, zirconium metal body), pressurised at 30 barg with hydrogen and heated to 100° C. for 5.5 hrs. During this period the autoclave was maintained at 30 barg with hydrogen from a gas ballast vessel. The reactants were allowed to stand overnight with the heating and stirring turned off The following day, the autoclave was de-pressurised, sampled and then purged with nitrogen. The reactor was then charged with hydrogen and the heating and stirring recommenced. The heating was stopped after a further 6.5 hrs (bringing the total of the heating time to 12 hrsat 100° C.) and the contents of the autoclave sampled again after cooling.

The samples were analysed by gas chromatography which showed that the hydrogenation of crotyl acetate had been driven to completion. This analysis also showed that the reaction was more than 85% selective to n-butyl acetate. The loss of reaction selectivity is believed to be due to the reversal of the butenyl acetate back to butadiene and acetic acid under the hydrogenation conditions which was catalysed by the presence of the acid. In spite of the closeness of the boiling points of crotyl acetate and n-butyl acetate, it was found that the hydrogenation products contained no detectable amounts of crotyl acetate. This is important since the odours of n-butyl acetate and crotyl acetate are very different and any significant amounts of crotyl acetate impurity in the product n-butyl acetate would be unacceptable.

Example 26

In this example, the effect of water on the reaction of butadiene and acetic acid in the presence of the Amberlyst 15® catalyst is investigated.

Experimental

The reactions described in this example were carried out in a 10 liter stainless steel autoclave. The ion-exchange resin Amberlyst 15® (85 g) was in this particular case washed with methanol (Soxhlet extraction), dried in vacuo at ca. 70° C. for six hours prior to use. The following were charged to the autoclave: acetic acid (3600 g), BHT (2,6-di-t-butyl-4-methylphenol, 3.0 g) and internal standard (n-decane, ca. 18 g). The desired amount of deionised water was then added to the acetic acid. The autoclave was then pressurised with $N_2$ and vented (three times). The reaction mixture was stirred (at ca. 1200 rpm), heated to the desired temperature (50° C.) and finally butadiene (700 g) was added. The progress of the reaction was monitored by GC analysis.

Figure 4A:
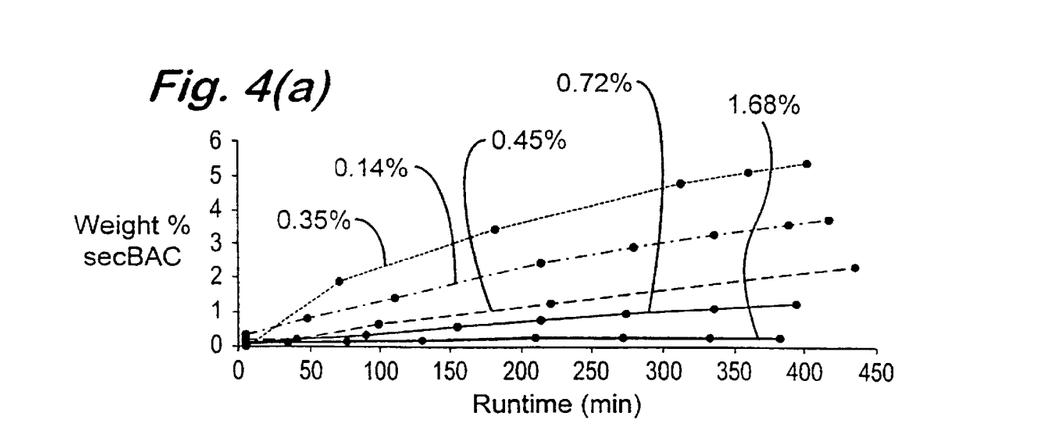
FIGS. 4a, 4b, 5a, 5b and 6 summarize the results obtained by varying the w/w/ % of water in acetic acid charge.
Figure 4B:
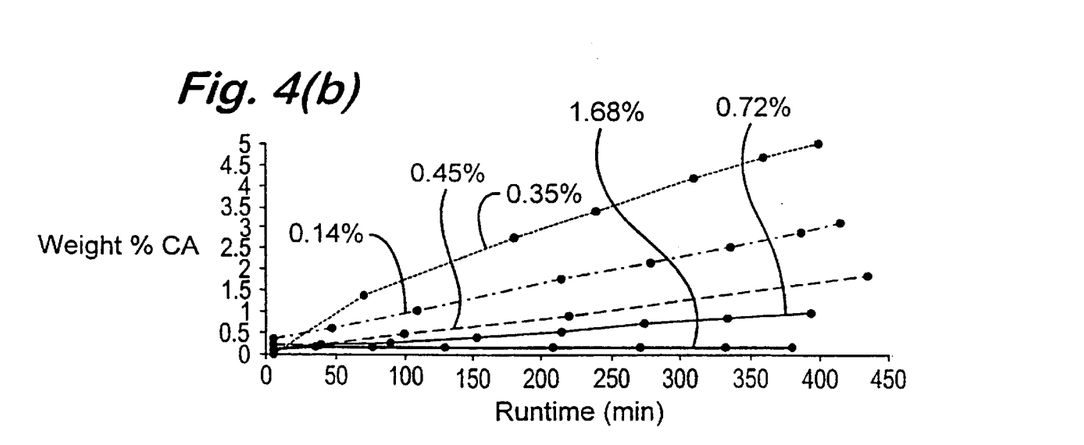
Figure 5A:
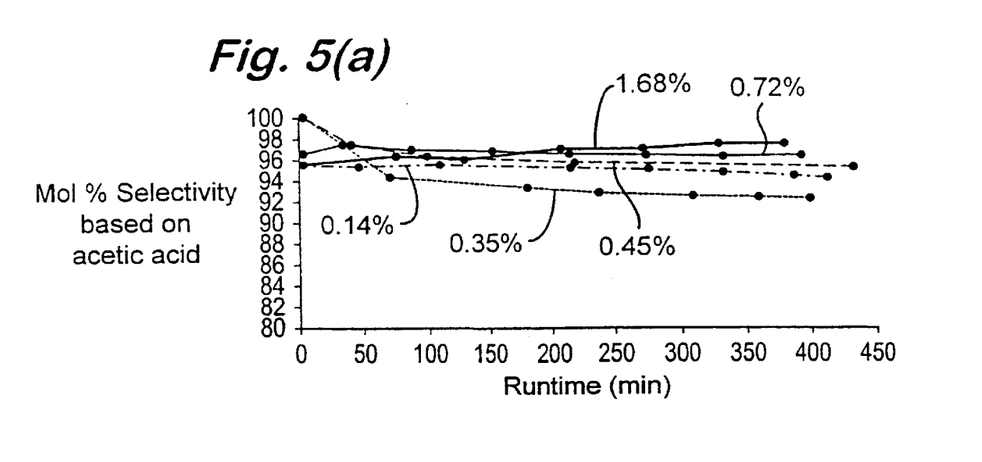
Figure 5B:
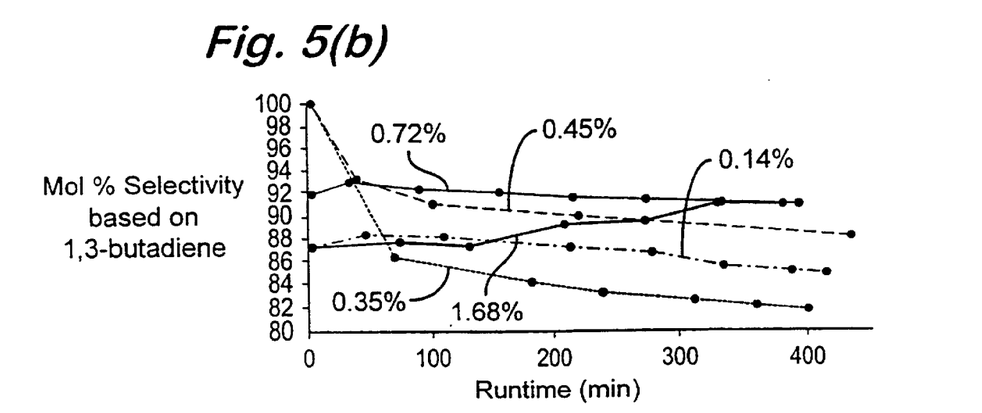
Figure 6:
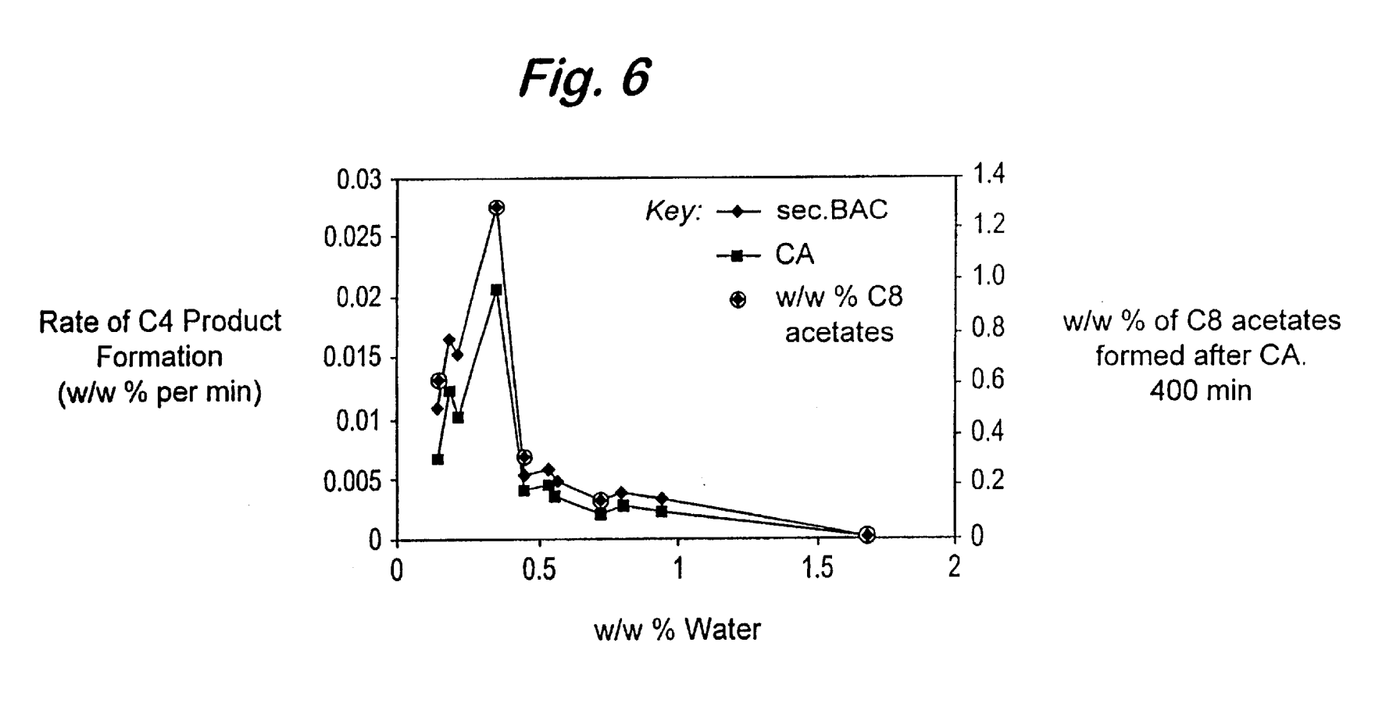

FIGS. 4–6 (see below) summarise the results obtained by varying the w/w % of water in acetic acid charge. The experiments described above show that the rate of reaction, the conversion of the starting materials and the selectivity towards the two product $C_4$-isomers, crotyl acetate and sec-butenyl acetate, was heavily affected by the water concentration during the individual autoclave reaction runs. The effect of water upon the reaction was explored ranging from 0.14% to 1.68% of w/w of water (based on the starting material acetic acid) and is illustrated in FIGS. 4 and 5.

The rate of $C_4$-isomer formation was estimated by linear regression (FIG. 4) and this analysis clearly identified 0.35% w/w water as the concentration which resulted in the fastest formation of both sec-butenyl acetate and crotyl acetate. This particular water concentration also led in the highest production of $C_4$-isomers at a total $C_4$ selectivity which was not significantly lower than those of the other water concentrations tested, especially when the much higher conversion of the starting materials was taken into consideration (see FIGS. 4 and 5).

Example 27

These examples investigated the use of triflic acid (trifluoromethanesulphonic acid) and triflate salts as catalysts for the addition reaction between butadiene and the saturated aliphatic carboxylic acid (step a)).

The experiments in this example were carried out in a 10 L stainless steel autoclave. The catalyst to be investigated was introduced into the autoclave as a solution in acetic acid. The reaction mixture was heated to the desired temperature. At the same time, a feed vessel was filled with the amount of 1,3-butadiene required and slightly pressurised with nitrogen. As soon as the autoclave reached the required temperature, 1,3-butadiene was added to the autoclave in one aliquot.

a) Triflic acid

The autoclave charge used is shown below:
Catalyst:—trifluoromethanesulphonic acid (triflic acid) 50 g.
Temp.:—50° C.
Charge: acetic acid 3668 g.
   BHT (inhibitor) 3.0 g.
   decane 72.1606 g.
Addition:—butadiene 705 g.

The table below shows the run results:

| | Triflic acid R6/1 | | | | | | | |
|---|---|---|---|---|---|---|---|---|
| | 1 | 2 | 3 | 4 | 5 | 6 | 7 | 8 |
| Component | Run time mins. | | | | | | | |
| % w/w | 5 | 50 | 99 | 168 | 200 | 252 | 321 | 354 |
| acetic acid | 72.50 | 84.12 | 82.38 | 82.87 | 81.68 | 80.95 | 81.22 | 81.16 |
| sec-butenyl acetate | 0.23 | 1.53 | 2.35 | 2.93 | 3.13 | 3.29 | 3.39 | 3.40 |
| C8 butadiene dimers | 0.18 | 0.07 | 0.13 | 0.20 | 0.23 | 0.22 | 0.31 | 0.32 |
| crotyl acetate | 3.06 | 1.50 | 2.68 | 3.56 | 3.90 | 4.26 | 4.40 | 4.42 |
| 4-vinyl cyclohexene | 0.10 | 0.10 | 0.09 | 0.09 | 0.08 | 0.08 | 0.08 | 0.07 |
| C8 acetates | 0.32 | 0.36 | 1.34 | 1.82 | 2.36 | 2.98 | 2.97 | 3.11 |
| C12 butadiene trimers | <0.01 | 0.16 | 0.03 | 0.05 | 0.06 | 0.06 | 0.18 | 0.16 | b) Lanthanide Triflates

Three trials were conducted, 1 2 and 3 (see below).

1) Catalyst:—ytterbium trifluoromethanesulphonate (ytterbium triflate) 60.2 g.
   Temp.:—50° C.
   Charge:—acetic acid 3676 g.
      bht (inhibitor) 3.0 g.
      decane 68.5285 g.
   Addition:—butadiene 700 g.

2) Catalyst:—ytterbium trifluoromethanesulphonate (ytterbium triflate) 60.2 g.
   Temp.:—135–145° C. (set 135° C.)
   Charge:—acetic acid 3676 g.
      bht (inhibitor) 3.0 g.
      decane 68.5285 g.
   Addition:—butadiene 700 g.+310 g.

3) Catalyst:—lanthanum trifluoromethanesulphonate (lanthanum triflate).
   Temp:—102° C.
   Charge:—acetic acid 3852 g.
      bht (inhibitor) 0 g.
      decane 0 g.
      lanthanum acetate 32.7 g.
      triflic acid 50 g.
   Addition:—butadiene 703 g.

The method outlined for triflic acid was followed except in trial 2) the autoclave was re-charged with the material from trial a). A fresh charge of butadiene was added. In trial 3 the lanthanum triflate was prepared in situ by adding lanthanum acetate and triflic acid (2.8 eq./La) as separate components to the charge. The results of the three trials are tabulated below:

| | trial no. | | |
|---|---|---|---|
| | 1 | 2 | 3 |
| Run time mins. | 236 | 241 | 251 |
| Component % w/w | | | |
| acetic acid | 80.65 | 83.65 | 77.24 |
| secondary butenyl acetate | 0.04 | 1.81 | 2.67 |
| C8 butadiene dimers | 0.01 | 0.11 | 0.16 |
| Crotyl acetate | 0.02 | 2.42 | 3.61 |
| 4-vinyl cyclohexene | 0.14 | 0.07 | 0.07 |
| C8 acetates | 0.01 | 1.07 | 1.93 |
| C12 butadiene trimers | <0.01 | 0.04 | 0.03 |

What is claimed is:

1. A process for making a butyl ester from butadiene, said process comprising a) reacting butadiene with a saturated aliphatic monocarboxylic acid in a reaction mixture containing water to form a mixture of n-butenyl and secondary butenyl esters, wherein the level of water in the reaction mixture is in the range from 0.05 to 5% w/w based on the carboxylic acid;

b) separating the n-butenyl ester from the secondary butenyl ester; and c) hydrogenating the n-butenyl ester separated in step b) in the presence of a catalyst to the corresponding n-butyl ester.

2. A process as claimed in claim 1, wherein the butadiene employed in step a) is in the form of a hydrocarbon mixture comprising butadiene.

3. A process as claimed in claim 1, the secondary butenyl ester separated in step b) is i) recycled to step a), ii) hydrogenated in the presence of a catalyst to produce sec-butyl ester, iii) thermally cracked to produce the starting butadiene and a saturated aliphatic monocarboxylic acid, or iv) further reacted.

4. A process as claimed in claim 1, wherein the carboxylic acid is acetic acid.

5. A process as claimed in claim 1, wherein step a) is carried out in the presence of a heterogeneous or homogeneous acidic catalyst.

6. A process as claimed in claim 5, wherein the catalyst is a heterogeneous catalyst in the form of an ion-exchange resin.

7. A process as claimed in claim 5, wherein the catalyst is a homogeneous catalyst in the form of triflic acid or a triflate salt.

* * * * *